United States Patent [19]

White et al.

[11] Patent Number: 4,976,736
[45] Date of Patent: Dec. 11, 1990

[54] COATED BIOMATERIALS AND METHODS FOR MAKING SAME

[75] Inventors: Eugene W. White, Rossiter, Pa.; Edwin C. Shors, Rancho Palos Verdes, Calif.

[73] Assignee: Interpore International, Irvine, Calif.

[21] Appl. No.: 345,194

[22] Filed: Apr. 28, 1989

[51] Int. Cl.$^5$ .............................................. A61F 2/28
[52] U.S. Cl. ..................................... 623/16; 427/2; 501/1; 433/201.1; 433/212.1; 606/77
[58] Field of Search .................... 427/2; 423/173, 175, 423/176; 501/1; 623/16, 66, 11; 433/222.1, 201.1, 212.1; 606/77

[56] References Cited
U.S. PATENT DOCUMENTS 3,929,971 12/1975 Roy .................................... 623/16 X
4,356,572 11/1982 Guillemin et al. ........... 433/201.1 X
4,917,702 4/1990 Scheicher et al. .................... 623/16

*Primary Examiner*—Alan W. Cannon
*Attorney, Agent, or Firm*—Cooper & Dunham

[57] ABSTRACT

Biomaterials useful for onthopedicanel dental applications is disclosed. These materials have a base portion of calcium carbonate and a surface layer of a synthetic phosphate such as hydroxyapatite. The base portion may be a calcium carbonate structure having three-dimensional interconnected porosity such as may be found in porous skeletal carbonate of marine life, e.g. coral porites skeletal aragonite, or it may be porous or non-porous granules of calcium carbonate.

A method for making the biomaterials is also disclosed. The synthetic phosphate surface is made using a hydroconversion reaction with a soluble or solubilized phosphate such as ammonium dibasic phosphate ($(NH_4)_2HPO_4$).

32 Claims, 1 Drawing Sheet

COATED BIOMATERIALS AND METHODS FOR MAKING SAME

BACKGROUND OF THE INVENTION

This invention relates to biomaterials useful in bone repair and replacement, especially as used for orthopedic, dental and oral surgery. More particularly, this invention relates to biomaterials having a special surface which resorbs more slowly than the underlying base.

Porous carbonate echinoderm or scleractinian skeletal material of marine life has a unique structure. This material has a uniformly permeable interconnected three dimensional porosity characterized by a substantially uniform pore volume in the range from about 10 to about 90%. The microstructure of this material resembles the cancellous structure characteristic of bony tissue or bone. Because of this unique microstructure of the porous carbonate echinoderm or scleractinian coral skeletal material of marine life, these materials are useful as bone substitutes. However, the carbonates of this material, such as provided in echinoid spine calcite and Porites skeletal aragonite, do not have the desired durability for use as bone substitutes.

A technique has been developed to convert the foregoing calcium carbonate coral materials to hydroxyapatite while at the same time retaining the unique microstructure of the coral material. U.S. Pat. No. 3,929,971 (incorporated herein by reference) discloses a hydrothermal exchange reaction for converting the porous carbonate skeletal material of marine life into a phosphate or hydroxyapatite skeletal material possessing the same microstructure as the carbonate skeletal material. These synthetic hydroxyapatite materials have been produced commercially and are available from Interpore International Inc., Irvine, Calif., under the tradename Interpore-200, which is derived from certain coral of the genus Porites, which have an average pore diameter of about 200 microns, and under the tradename Interpore-500 derived from certain members of the family Goniopora, which have pore diameters of about 500 microns.

Interpore-200 and Interpore-500, have also been identified as replamineform hydroxyapatite and coralline hydroxyapatite, have been found to be useful as bone substitute materials in dental and surgical applications. These materials are essentially nondegradable. More information concerning these materials can be found in the article by Eugene White and Edwin C. Shors entitled "Biomaterial Aspects of Interpore-200 Porous Hydroxyapatite", which appeared in *Dental Clinics of North America*, Vol. 30, No. January 1986, pp. 49–67, incorporated herein by reference.

However, while calcium phosphates such as Interpore-200 and Interpore-500 are satisfactory for many applications, and promote the ingrowth of bone and other tissue into and around the implant, they do not satisfy all of the needs of surgeons using them as bone replacements or implants.

For some applications, surgeons prefer that bone substitutes resorb within a few weeks or months following implantation, after new bone has grown through the implant site. One approach to increase the degradation rate of ceramic implants has been to use tricalcium phosphate instead of hydroxyapatite. Tricalcium phosphate degrades, but its rate of degradation is inconsistent and unpredictable. Another approach utilizes polymers that are biodegradable and non-toxic to the host into whom the polymer is implanted. However, there is little evidence that these materials are osteoconductive or have adequate interconnected porosity.

Accordingly, it is an object of this invention to provide a ceramic biomaterial which degrades in a predictable manner and at an acceptable rate.

It is another object of this invention to provide bone substitute materials and methods for their manufacture derived from solid or porous calcium carbonate and having a surface layer of hydroxyapatite.

It is a further object of this invention to provide bone substitute materials derived from coral having the unique porous microstructure thereof, while having a more slowly resorbing layer of calcium phosphate or hydroxyapatite.

It is a still further object of the invention to provide bone substitute materials which include a calcium phosphate layer throughout the porous structure of coral without compromising the porosity of the structure or its interconnectedness.

It is another object of the invention to provide solid or porous calcium carbonate granules having calcium phosphate surface regions.

It is a further object of the invention to provide a degradable biomaterial which provides an adherent surface for growth factors and antibiotics.

How these and other objects of this invention are achieved will become apparent in light of the accompanying disclosure.

SUMMARY OF THE INVENTION

The present invention is directed to an improved biomaterial which can support bone ingrowth but which will degrade at a controlled rate, allowing bone to fill the voids left by the degrading implant.

According to the invention, a biomaterial is provided which has a base portion of calcium carbonate and a surface layer of calcium phosphate or hydroxyapatite. Preferably the calcium carbonate is porous throughout and is derived from coral skeletal material. The calcium carbonate at the surface of a coral skeletal sample is converted to calcium phosphate preferably by a hydrothermal chemical exchange reaction with a phosphate such as ammonium phosphate. The phosphate or hydroxyapatite surfaced calcium carbonate biomaterial may be used to replace portions of the bony animal skeletal structure, such as bone implants and prostheses and dental implants and prostheses, or any application where a resorbable implant seems advantageous.

Alternatively, the present invention can be practiced by providing granules of the phosphate or hydroxyapatite surfaced calcium carbonate biomaterial having diameters of about 400 microns to about 5 mm. The granules may be derived from porous coral or other marine life or may be essentially non-porous granules whose surface is converted to phosphate or hydroxyapatite by a hydrothermal conversion process.

In some applications, the pores of the phosphate or hydroxyapatite surfaced calcium carbonate biomaterial derived from skeletal marine life such as coral can be filled with a biocompatible polymer. The polymer may itself be degradable by the host into which it is implanted or it may be nondegradable, depending on the proposed use. Degradable polymers preferably include polyglycolic acid or polylactic acid, while nondegradable polymers may include polysulfones, silicone rubber, polyurethane, ultrahigh molecular weight polyethylene, or other polymers known to be nontoxic and implantable in humans. In some uses, it may be advantageous after filling the pores with the polymer to remove the phosphate or hydroxyapatite layer on the outer surface of the biomaterial to expose the calcium carbonate and dissolve away some or all of the calcium carbonate to form a porous hydroxyapatite and polymer biomaterial.

Preferably, the biomaterials of the present invention are made by converting the surface of a calcium carbonate sample to calcium phosphate, in the crystalline form hydroxyapatite. The conversion is accomplished by a hydrothermal chemical exchange with a phosphate, such as ammonium phosphate, and the thickness of the phosphate layer on the surface of the calcium carbonate may be controlled by varying the concentration of the phosphate employed in the process.

The invention, together with further objects and attendant advantages, will be best understood by reference to the following detailed description taken in conjunction with the accompanying drawing.

DESCRIPTION OF THE PREFERRED EMBODIMENT

Figure 1:
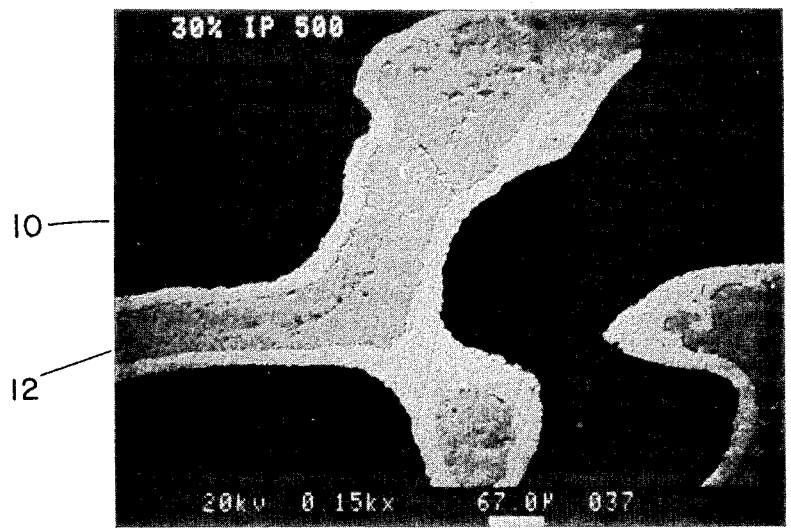
FIG. 1 is a rendering of an actual photomicrograph (magnified 150×) of a section of biomaterial of this invention showing the calcium carbonate base portion and calcium phosphate or hydroxyapatite surface layer.

Hydroxyapatite is widely used as a bone substitute material in oral, periodontal and craniofacial surgery, and is under investigation for various orthopedic applications, such as bone replacements due to trauma, spinal fusions, tumors, joint surgery and the like. The biocompatibility of hydroxyapatite is well established and it is available commercially, mostly for oral surgery applications, in dense and porous forms. Hydroxyapatite promotes bone ingrowth in and around the implant, but even the porous form is resorbable only at a rate of 1-2 percent annually. Dense hydroxyapatite is essentially nonresorbable over a period of years.

In accordance with the present invention, the surface carbonate making up the microstructure of porous permeable animal carbonate skeletal material, such as the porous, permeable carbonate skeletal material of marine life, e.g. the porous skeletal material of marine invertebrates, such as echinoid spine calcite, Porites skeletal aragonite and Goniopora skeletal aragonite (both calcite and aragonite being carbonates) has been converted into whitlockite and hydroxyapatite by hydrothermal chemical exchange with a phosphate. The resulting produced synthetic phosphate (hydroxyapatite or whitlockite) surfaced skeletal material possesses substantially the same microstructure of the original carbonate skeletal material from which it was derived. These synthetic materials are useful for the manufacture of prosthetic devices, such as body and bone implants, tooth fixation, massive hard tissue replacements and the like since hydroxyapatite and whitlockite are biocompatible materials.

The thin layer of hydroxyapatite resorbs slowly after allowing bone and other tissue to grow into the pores during an initial repair period during which the surrounding bone can form a repair network. After the hydroxyapatite resorbs enough to expose the underlying base of calcium carbonate, the degradation process speeds up owing to the more rapid degradation of calcium carbonate as compared with hydroxyapatite. This allows even more bone ingrowth to occur, eventually permitting complete replacement of the artificial part with new bone and other tissue.

Whitlockite seems to degrade more rapidly than hydroxyapatite, and whitlockite surfaced calcite structures may be used where more rapid initial degradation is desired. However, it is preferred that the rate of degradation be modulated or controlled by varying the thickness of the hydroxyapatite coating which can be conveniently accomplished by varying the concentration of the phosphate solution used in the conversion process.

The synthetic phosphate materials prepared in accordance with this invention, as indicated hereinabove, are particularly useful as biomaterials for use in the manufacture of prosthetic devices or for use as implants in human hard tissue and the like. The surface of the materials of this invention, particularly those made from porous carbonate (aragonite) skeletal material of marine life, since they are comprised predominantly of hydroxyapatite $Ca_{10}(PO_4)6(OH)_2$ with some carbonate ($CO_3$) present, approximate the composition of the inorganic component of human hard tissue, i.e., human bone. This hydroxyapatite surface has osteophilic and osteoconductive properties, and helps promote the growth of bone tissue into the porosity of the biomaterial.

Materials of this invention would preferably have a microstructure which is porous, completely interconnected, approximating the same pore size as cancellous human bone which would allow permeation of body fluids and blood cells thereinto. Materials in accordance with this invention could be prepared which would be suitable for root portions of tooth implants and mandibular restorations where it would permit rapid ingrowth of periodontal and hard tissue, as well as other bone repair functions such as segmental bone replacements for bone fractures, tumors, joint surgery and spinal fusion.

As indicated, various porous carbonate skeletal materials, particularly porous carbonate skeletal material of marine life, may be employed in the practices of this invention. Particularly useful, because of the vast quantities available, is the carbonate skeletal material of scleractinian coral Porites wherein the skeletal material is composed of the carbonate aragonite, and the average pore size is approximately 200 microns. Other corals of the genera Goniopora, Alveopora, Acropora and others may be suitable employed in the practice of this invention as the source of the carbonate skeletal material for conversion by hydrothermal chemical exchange with a phosphate into hydroxyapatite. Goniopora has an average pore size of about 500 microns, and includes pores ranging in size from 5 microns to about 1000 microns.

Where the carbonate skeletal material is made up of a calcite carbonate marine skeletal material, such as echinoid spine calcite where the calcite contains a substantial amount of magnesium associated therewith, whitlockite is produced upon hydrothermal chemical exchange with a phosphate on the surface of the biomaterial. Both materials, however, hydroxyapatite and whitlockite, are useful materials, with the hydroxyapatite being preferred for the manufacture of a prosthetic device and the like.

Alternatively, the biomaterials of the present invention can be made in the form of porous or nonporous granules having a surface layer of hydroxyapatite (or whitlockite) on a base of porous or solid calcium carbonate. These granules can be dispensed into a cavity where bone repair is desired using a syringe adapted to deliver the particles into the cavity. The irregular surfaces of the particles create spaces between adjacent ones, permitting bone and other tissue to grow around the particles, and in the case of porous particles, into their pores. The particles of the present invention are particularly useful for dental application such as reconstruction of the aveolar ridge and for filling periodontal spaces. For periodontal use, granules having an average nominal diameter of about 425–600 microns and an average pore size of about 200 microns should be used; for reconstruction of the aveolar ridge, granules having an average nominal diameter of about 425 to 1000 microns and an average pore size of about 200 microns can be used. For orthopedic applications, larger granules having an average nominal diameter of 1–2 mm or 3–5 mm can be used.

In the manufacture of the synthetic materials of this invention it would be desirable, before subjecting the naturally occurring porous carbonate skeletal material to hydrothermal chemical exchange with a phosphate, to first prepare the porous carbonate skeletal material by the removal of any organic material therefrom. A suitable technique for the removal of organic material from the porous skeletal material would be by immersion in a dilute (about 5%) aqueous solution of sodium hypochlorite. Usually an immersion time of about 30 hours is satisfactory for the removal of substantially all of the organic matter. Following this the material is rinsed, preferably in deionized water, and dried, such as at a temperature of about 90° C. Any suitable technique for the removal of organic material, such as the technique for the removal of organic matter from animal bone described in SCIENCE, 119, 771 (1954), might be employed If desired, the organic-free carbonate skeletal material after conversion by hydrothermal chemical exchange with a phosphate to hydroxyapatite or whitlockite, if not already shaped, may be shaped into a desired form or structure, for example, cylinders, screws, nuts, bolts, pins, flat or curved plates and the like.

The conversion of porous carbonate skeletal materials into the phosphate surfaced carbonate biomaterials of the present invention preferably involves lower temperature and pressures than those disclosed in U.S. Pat. No. 3,929,971. The conversion may be carried out by placing blocks or granules of calcium carbonate in phosphate solution or by freeze drying the phosphate onto the carbonate base and then carrying out the hydroconversion in a steam filled autoclave. Preferred temperatures range from about 200°–250° C., with about 200°–230° C. appearing optimum. Preferably, the pressure should be that developed in a sealed vessel or autoclave by the steam contained therein, which is estimated to be about 500 to about 4000 p.s.i. If the conversion is carried out in a phosphate solution, such as ammonium phosphate, the temperature should preferably be about 230° C. and the pressure should be preferably about 1000 p.s.i., and the reaction should be carried out for about 10 to about 60 hours.

The chemical reaction involved in the conversion of calcium carbonate to hydroxyapatite is as follows:

$$10\ CaCO_3 + 6(NH_4)_2HPO_4 + 2HO_2$$

$$Ca_{10}(PO_4)_6(OH)_2 + 6\ (NH_4)_2CO_3 + 4H_2CO_3$$

Various substantially water-soluble phosphates may be employed as the phosphate contributing reactant in the hydrothermal chemical exchange reaction to produce the special materials of this invention. The preferred phosphates include ammonium phosphates and orthophosphates. Also useful would be the calcium orthophosphates and the acid phosphates, as well as orthophosphoric acid including its hydrates and derivatives and mixtures of a weak acid, such as acetic acid, with a phosphate.

Other orthophosphates and acid phosphates useful in the practices of this invention include $Li_3(PO_4)$, $LiH_2(PO_4)$, $Na_3(PO_4)$, $Na_2HPO_4$, $Na_3H_3(PO_4)_2$, $NaH_2(PO_4)$, $Na_4H_5(PO_4)_3$, $NaH_5(PO_4)_2$, $K_3PO_4$, $K_2HPO_4$, $K_7H_5(PO_4)_4$, $K_5H_4(PO_4)_3$, $KH_2(PO_4)$, $KH_5(PO_4)_2$, $(HN_4)_3PO_4$, $(NH_4)_2HPO_4$, $NH_4H_2PO_4$, $NH_4H_5(PO_4)_2$, $NH_4H_8(PO_4)_3$, and their hydrates, and mixed salts especially of K, $NH_4$ and Na orthophosphates and acid phosphates, including also Rb and Cs orthophosphates and acid phosphates. Also useful in addition to the aforementioned are the calcium orthophosphates $2CaO.P_2O_5$, $CaHPO_4$, $Ca_4P_2O_9$, $Ca(H_2PO_4)_2$ and $CaO.P_2O_5$.

Upon completion of the hydrothermal chemical exchange reaction it has been shown by examination including optical microscopy and scanning electron microscopy, that the resulting three-dimensional completely interpenetrating porous structure is the same as the original carbonate structure from which it was derived. The original calcium carbonate (aragonite) crystal structure of the resulting produced material is absent as determined by x-ray diffraction and by optical microscopy.

The following is illustrative of the preferred methods of making the biomaterials of the present invention. A cylinder ⅜ inch diameter by one inch was machined from a head of Porites coral. The Porites coral cylinder was cleaned ultrasonically to remove machining debris then rinsed and dried. The dried cylinder weighed 16.7 gm and fit into the Teflon liner of a test size reaction vessel To the dry Teflon liner (87.0 gm) was added 7.6 gm distilled $H_2O$ and 5.6 gm $(NH_4)_2HPO_4$. The Teflon liner and contents were preheated in 80° C. oven and contents stirred to dissolve phosphate. The coral cylinder prepared above was lowered into the 80° C. solution, the Teflon liner with contents was placed in preheated stainless steel vessel and sealed. The sealed vessel was placed in a 220° C. oven and held at 220° C. for 12 hours. The vessel was allowed to cool down after which it was opened. After rinsing in distilled water and drying, the weight of hydroxyapatite-coated coral was 16.4 gm. Stereoptic microscope examination revealed excellent pore fidelity and no cracks.

In another variation of the method, samples of coral, either Porites or Goniopora are cut with dimensions varying from 8 mm×8 mm×3 mm to 30 mm×70 mm×x 15 mm rods or any other desired shape. The coral is cleaned by immersion in standard chlorine bleach (sodium hypochlorite) for 24 hours, then rinsed several times in water, and then completely dried. The blocks of coral are then weighed.

Solutions of ammonium dibasic phosphate ((NH$_4$)$_2$HPO$_4$)) approximately 5-40 percent by weight (Baker Chemicals, Catalog #0784-05) are made by dissolving the salt in deionized water. The dry blocks of coral are individually weighed and placed in separate polyethylene bags with sealable tops. An ammonium phosphate solution is then piped into the bags to totally immerse the blocks. The bags are transferred to a vacuum chamber and the blocks are degassed to fully infiltrate the solution into the pores. The tops to the bags are then closed, making sure that the blocks remain fully submerged. The bags are then transferred to a conventional freezer (approximately 15° C.) for approximately 24 hours to freeze the blocks. The frozen blocks and solution are then removed from the bags and placed in a freeze-drying chamber. Freeze-drying is performed in a vacuum (less than 0.1 Torr) at a temperature of 35° C. for at least 24 hours. The excess dried ammonium phosphate crust around the blocks is then removed from the surface by scraping. The blocks are weighed and the percent weight gain is determined.

Carbonate to phosphate substitution by hydrothermal conversion is then performed using a 750 ml high pressure autoclave (Berghof America, Catalog #7400) having a Teflon liner, filled with approximately 200 ml of deionized water. A Teflon platform is placed on the bottom of the liner such that the upper surface is above the waterline. The blocks are then stacked on the platform with Teflon webbing acting as a spacer between successive layers of the blocks. Species of coral and concentrations of ammonium phosphate can be mixed without cross-contamination. The top to the conversion vessel is closed and the vessel is placed in a conventional convection oven (Blue M, Catalog #POM7-136F-3). The temperature is gradually raised to 230° and held there for about 60 hours. A pressure of about 1000 psi is generated by the vapor pressure of steam and the reactants at the stated temperature. At completion of the hydrothermal conversion, the reaction vessel is opened and blocks removed. The thickness of the coating has been observed to be directly proportional to the concentration of ammonium phosphate solution used at the immersion step and to the weight gain for each of the two species of coral. The Goniopora coral results in a thicker coating than the Porites coral for the same concentration of ammonium phosphate, because the Goniopora has a larger void fraction and a smaller specific surface area.

The thickness of the hydroxyapatite-coating is dependent on the concentration of ammonium phosphate used with the freeze dried treatment. The thicknesses of the coating achieved experimentally on Porites coral are:

| % HA Solution | Thickness of Coating ($\mu$m) | Range ($\mu$m) |
| --- | --- | --- |
| 5% | 0.8 | 0.6-1.2 |
| 10% | 2.0 | 1.2-2.5 |
| 20% | 3.4 | 3.1-3.8 |
| 30% | 4.7 | 3.7-5.6 |
| 40% | 6.19 | 6.2-7.5 |

The thickness on the Goniopora coral is a follows:

| % Ammonium Phosphate | Thickness of Coating | Range ($\mu$m) |
| --- | --- | --- |
| 5% | 3.8 | 3.1-4.4 |
| 10% | 5.6 | 5.0-6.3 |
| 20% | 10.6 | 10.0-11.2 |
| 30% | 13.7 | 12.5-15.0 |
| 40% | 20.6 | 18.7-22.5 |

A biomaterial made in accordance with this process was embedded in a suitable medium (Spurr's Embedding Medium) and polished. FIG. 1 is an example of a photomicrograph from a scanning electron microscope with backscatter detector illustrating as sample of a porous biomaterial made from Porites coral. A distinct surface layer of phosphate 10 was present on all surfaces of the calcium carbonate 12, and appeared uniform throughout the structure. The thickness of the hydroxyapatite layer 10 was directly proportional to the concentration of the ammonium dibasic phosphate solution used to fabricate the biomaterial. The unique porous microstructure of the coral was preserved.

To determine the composition of a sample of the biomaterial, energy dispersive x-ray analysis was performed on the hydroxyapatite surface layer and the calcium carbonate core of a sample made with Goniopora coral and 30% ammonium dibasic phosphate solution. The results from the analysis of the hydroxyapatite surface layer or region are set forth in the accompanying Table 1, while the results from analysis of the calcium carbonate core are set forth in the accompanying Table 2. These tests demonstrated that the surface layer was rich in phosphate (about 47%), whereas the center core of coral material had essentially no phosphate.

TABLE 1

| Center Core Analysis | |
| --- | --- |
| Accelerating voltage | 20.0 KeV |
| Beam - sample incidence angle | 70.0 degrees |
| Xray emergence angle | 29.4 degrees |
| Xray - window incidence angle | 9.1 degrees |
| Window thickness | 12.0 microns |

| STANDARDLESS EDS ANALYSIS (ZAF CORRECTIONS VIA MAGIC V) | | | | | |
| --- | --- | --- | --- | --- | --- |
| ELEMENT & LINE | WEIGHT PERCENT | ATOMIC PERCENT* | PRECISION 3 SIGMA | K-RATIO** | ITER |
| P KA | 0.36 | 0.46 | 0.11 | 0.0028 | |
| Ca KA | 99.84 | 99.54 | 0.51 | 0.9972 | 2 |
| TOTAL | 100.00 | | | | |

*NOTE: ATOMIC PERCENT is normalized to 100
**NOTE: K-RATIO = K-RATIO × R
where R - reference(standard)/reference(sample)
NORMALIZATION FACTOR: 0.998

TABLE 2
Surface Analysis

| | |
|---|---|
| Accelerating voltage | 20.0 KeV |
| Beam - sample incidence angle | 70.0 degrees |
| Xray emergence angle | 29.4 degrees |
| Xray - window incidence angle | 9.1 degrees |
| Window thickness | 12.0 microns |

STANDARDLESS SKS ANALYSIS (ZAF CORRECTIONS VIA MAGIC V)

| ELEMENT & LINE | WEIGHT PERCENT | ATOMIC PERCENT* | PRECISION 3 SIGMA | K-RATIO | ITER |
|---|---|---|---|---|---|
| P KA | 34.96 | 41.02 | 0.38 | 0.3364 | |
| Ca KA | 65.04 | 58.98 | 0.49 | 0.6636 | 4 |
| TOTAL | 100.00 | | | | |

*NOTE: ATOMIC PERCENT is normalized to 100
**NOTE: K-RATIO = K-RATIO × R
where R = reference(standard)/reference(sample)
NORMALIZATION FACTOR: 0.882

To make coatings on granules, granules of either solid calcium carbonate (Mallinkrodt Chemicals, Catalog 6210) or porous calcium carbonate derived from corals (Porites, 425-1000 μm in diameter and Goniopora, 0.5 mm in diameter) are placed in plastic bags as described above. The ammonium phosphate $((NH_4)_2HPO_4)$ is added, frozen and freeze-dried. Hydrothermal conversion is accomplished by placing the freeze-dried granules in porous Teflon bags or in separate Teflon beakers, and then heating the sample in a closed container as discussed above.

Another embodiment of the present invention combines the osteophyllic and osteoconductive properties of hydroxyapatites with biocompatible polymers used as implants. A hydroxyapatite coated porous calcium carbonate composite is prepared as described above. The porosity of the composite is filled with polymer either with positive injection pressure or by vacuum impregnation. Examples of polymers suitable for the practice of this invention include polysulfone, polyethylene, such as ultrahigh molecular weight polyethylene, silicone rubber (Dow Corning) or polyurethane (Thermedics Inc., Tecoflex).

After solidification of the polymer, the composite may optionally be trimmed on all surfaces to expose the calcium carbonate structure. The composite is then immersed in 10% acetic acid. This preferentially dissolves the calcium carbonate leaving behind the hydroxyapatite and polymer. An interconnected porous structure remains that is lined with hydroxyapatite and has an infrastructure of the polymer. Alternatively, the calcium carbonate is not dissolved away, or only partially dissolved away. After implantation in the body, however, the body preferentially degrades the calcium carbonate leaving the hydroxyapatite coating which degrades more slowly and the polymer.

In another embodiment, the porosity of the hydroxyapatite coated composite may be filled with a polymer which may be degraded by the body after implantation. Examples of such polymers include polylactic, polyglycolic acid or polycaprolactone (Union Carbide). With implants made in accordance with this embodiment, the calcium carbonate may be removed or left intact, depending upon the desired properties of the implant. The polymer in such an implant degrades after implantation, as does the calcium carbonate, when present. The dissolution of polymer and calcium carbonate provides additional space for bone or tissue ingrowth.

The biomaterials of the present invention provide several important and unique advantages. The hydroxyapatite surface layer degrades slowly as compared to calcium carbonate and helps modulate degradation. The implant will degrade only slowly at first, allowing the bone or other tissue to fill the interconnected porous network. Thus ingrowth can occur prior to resorbtion.

Figure 2:
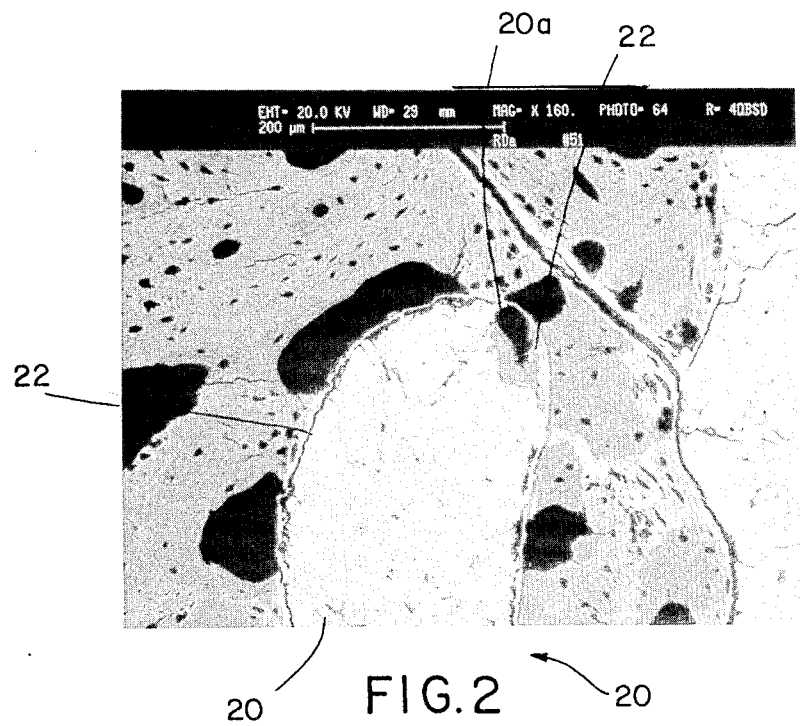
FIG. 2 is a rendering of an actual photomicrograph (160×) showing a cross-section of an implant made from the biomaterial of this invention that had been implanted several months earlier in an animal.

FIG. 2 illustrates an implant 18 of the biomaterial of the present invention made by hydroconversion of Goniopora with 5% ammonium phosphate, which was implanted for approximately 12 weeks in a rabbit tibia. The implant 18 includes the calcium carbonate base 20 and the hydroxyapatite or phosphate surface 22 surrounded by bone 24. As shown in FIG. 2, once cracks or fissures appear in the hydroxyapatite surface 22 exposing the underlying calcium carbonate 20, degradation accelerates since calcium carbonate appears to degrade more rapidly than does hydroxyapatite. Bone 24 can be seen replacing the space 20a formerly filled with calcium carbonate 20.

Another advantage of the hydroxyapatite layer in the biomaterial of the present invention is its inherent osteophilic nature. That is, hydroxyapatite on the surface of a porous implant seems to promote bone ingrowth into the pores of the implant, whereas calcium carbonate seems not to possess this property Another advantage of hydroxyapatite is absorbency, which may explain its ability to bind other compositions which aid in the bone repair process. An antibiotic such as tetracycline, oxytetracycline or other known synthetic or semisynthetic antibiotic may be introduced unto the pore cavities of the implant. Likewise, one of several growth factors such as transforming growth factor or one of the Bone Morphogenic Proteins can be attached which help promote bone ingrowth. For example, transforming growth factor $\beta$ (TGF-$\beta$) is believed to have a role in transforming undifferentiated primitive mesenchymal cells observed at the leading edge of bone ingrowth into bone cells. TGF-$\beta$ can be added to the hydroxyapatite surface after hydroconversion to help enhance bone ingrowth. Alternatively, growth factor or an antibiotic can be intermixed with a preferably biodegradable polymer and injected or vacuum infiltrated into the porosity of the phosphate surfaced carbonate biomaterial.

Of course, other modifications, alterations and substitutions may be apparent to those skilled in the art in light of the foregoing disclosure. For example, the hydroxyapatite surface layer can be accomplished by a method other than hydroconversion. Therefore it is intended that the scope of the invention be governed by the following claims.

What is claimed is:

1. A biomaterial comprising a base portion consisting essentially of calcium carbonate and having a surface layer of synthetic phosphate.

2. A biomaterial as recited in claim 1 having a three dimensional porous microstructure corresponding to the microstructure of porous carbonate echinoderm or schleractinian coral skeletal material.

3. A biomaterial as recited in claim 1 wherein said surface layer has a thickness less than about 25 microns.

4. A biomaterial as recited in claim 2 wherein said base portion is porous calcium carbonate derived from coral.

5. A biomaterial as recited in claim 4 wherein said surface layer is made by converting the surface of said calcium carbonate base portion to hydroxyapatite.

6. A biomaterial as recited in claim 2 wherein said base portion is Porites coral and said surface layer consists essentially of hydroxyapatite.

7. A biomaterial as recited in claim 2 wherein said base portion is Goniopora or Alveolopora coral and said surface layer consists essentially of hydroxyapatite.

8. A biomaterial as recited in claim 1 wherein said base portion is solid calcium carbonate.

9. A biomaterial as recited in claim 6 having an average pore diameter of about 200 microns.

10. A biomaterial as recited in claim 7 having an averagepore diameter of about 500 microns.

11. A biomaterial as recited in claim 2 having pore sizes in the range of about 5-1000 microns.

12. A biomaterial as recited in claim 2 wherein said base portion is Porites or Goniopora coral and said surface layer is made by converting calcium carbonate to calcium phosphate.

13. A biomaterial in accordance with claim 2 having substantially uniform pore connections or openings in the range from about 5 microns to about 1000 microns.

14. A biomaterial in accordance with claim 1 wherein the synthetic phosphate is hydroxyapatite or whitlockite.

15. A biomaterial in accordance with claim 2 wherein said base portion is coral skeletal aragonite and said surface layer consists essentially of hydroxyapatite.

16. A biomaterial in accordance with claim 15 wherein said coral skeletal aragonite is Porites skeletal aragonite.

17. A biomaterial in accordance with claim 1 wherein said base portion is a calcium carbonate granule.

18. A biomaterial in accordance with claim 17 wherein said base portion is solid.

19. A biomaterial in accordance with claim 17 wherein said calcium carbonate granule is porous and is derived from coral.

20. A biomaterial in accordance with claim 17 wherein the diameter of said granule ranges from about 425 microns to about 5 millimeters.

21. A biomaterial in accordance with claim 20 wherein the average diameter of said granule ranges from about 425 microns to about 600 microns.

22. A biomaterial as recited in claim 2 wherein said base portion is derived from porous echinoderm skeletal material and said surface layer consists essentially of whitlockite.

23. A synthetic biomaterial characterized by a substantially uniform pore volume in the range from about 10% to about 90% and having a microstructure characterized by a pronounced three dimensional fenestrate structure corresponding to the microstructure of the porous carbonate echinoderm or schleractinian coral skeletal material of marine life and providing a periodic minimal surface, said periodic minimal surface dividing the volume of said material into two interpenetrating regions, each of which is a single, multiply connected domain, said material having a substantially uniform pore size diameter and substantially uniform pore connection or openings in the range from about 5 microns to about 1000 microns, said synthetic material comprising a base portion of calcium carbonate and a surface layer of calcium phosphate.

24. A biomaterial in accordance with claim 23, wherein said biomaterial has the microstructure of echinoderm skeletal calcite and surface layer consists essentially of whitlockite.

25. A biomaterial in accordance with claim 23 having the microstructure of coral skeletal aragonite and said surface layer consists essentially of hydroxyapatite.

26. A biomaterial in accordance with claim 25 wherein said coral skeletal aragonite is Porites skeletal aragonite.

27. A biomaterial in accordance with claim 23 having the microstructure of Alveolopora or Goniopora skeletal aragonite and wherein said surface layer consists essentially of hydroxyapatite.

28. A biomaterial in accordance with claim 23 wherein the microstructure has the ratio of pore volume to the volume of solid of approximately 1 and has a cross-sectional diameter of both the pore and solid phase of about the same dimension ranging from about 5 microns to about 1000 microns.

29. A biomaterial in accordance with claim 23 having pore sizes in the range from about 40 to about 250 microns.

30. A biomaterial in accordance with claim 23 wherein said biomaterial is shaped or formed into a shape commensurate with a bone repair or replacement function.

31. A biomaterial in accordance with claim 30 wherein said phosphate surfaced calcium carbonate biomaterial is hydroxyapatite surfaced calcium carbonate.

32. A biomaterial in accordance with claim 23 having an average pore size of about 500 microns.

* * * * *